United States Patent
Dubois et al.

(10) Patent No.: US 9,567,293 B2
(45) Date of Patent: Feb. 14, 2017

(54) COMBINED SYNTHESIS OF A NITRILE-ESTER/ACID AND OF A DIESTER/DIACID

(71) Applicant: ARKEMA FRANCE, Colombes (FR)

(72) Inventors: Jean-Luc Dubois, Millery (FR); Jean-Luc Couturier, Lyons (FR); Markus Brandhorst, Lyons (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/766,951

(22) PCT Filed: Feb. 10, 2014

(86) PCT No.: PCT/FR2014/050247
§ 371 (c)(1),
(2) Date: Aug. 10, 2015

(87) PCT Pub. No.: WO2014/122410
PCT Pub. Date: Aug. 14, 2014

(65) Prior Publication Data
US 2016/0016894 A1    Jan. 21, 2016

(30) Foreign Application Priority Data
Feb. 8, 2013    (FR) ..................................... 13 51102

(51) Int. Cl.
| | | |
|---|---|---|
| C08G 69/00 | (2006.01) | |
| C07C 253/30 | (2006.01) | |
| C08G 69/04 | (2006.01) | |
| C07C 69/65 | (2006.01) | |
| C07C 67/475 | (2006.01) | |
| C07C 51/285 | (2006.01) | |
| C07C 51/09 | (2006.01) | |
| C07C 227/04 | (2006.01) | |
| C08G 69/08 | (2006.01) | |
| C07C 69/602 | (2006.01) | |
| C08F 132/06 | (2006.01) | |
| C11B 3/00 | (2006.01) | |
| C08F 8/46 | (2006.01) | |

(52) U.S. Cl.
CPC ............. *C07C 253/30* (2013.01); *C07C 51/09* (2013.01); *C07C 51/285* (2013.01); *C07C 67/475* (2013.01); *C07C 69/65* (2013.01); *C07C 227/04* (2013.01); *C08G 69/04* (2013.01); *C08G 69/08* (2013.01); *C07C 69/602* (2013.01); *C08F 8/46* (2013.01); *C08F 132/06* (2013.01); *C11B 3/00* (2013.01)

(58) Field of Classification Search
CPC .......... C08F 8/46; C08F 132/06; C08G 69/08; C08G 69/04; C11B 3/00; C07C 69/65; C07C 69/602
See application file for complete search history.

(56) References Cited

U.S. PATENT DOCUMENTS

| | | | |
|---|---|---|---|
| 2,813,113 A | 11/1957 | Goebel et al. | |
| 2010/0168453 A1 | 7/2010 | Dubois | |
| 2010/0196973 A1 | 8/2010 | Dubois | |
| 2011/0224454 A1 | 9/2011 | Dubois | |
| 2011/0300590 A1 | 12/2011 | Dubois | |
| 2012/0011765 A1* | 1/2012 | Dubois | ..................... C10L 1/02 44/384 |
| 2014/0148607 A1 | 5/2014 | Dubois | |
| 2014/0155647 A1 | 6/2014 | Dubois | |

FOREIGN PATENT DOCUMENTS

| | | |
|---|---|---|
| FR | 2 912741 A1 | 8/2008 |
| FR | 2 941 694 A1 | 8/2010 |
| FR | 2 984 309 A1 | 6/2013 |
| GB | 741 739 A | 12/1955 |
| GB | 743 491 A | 1/1956 |
| WO | WO 2008/104722 A2 | 9/2008 |
| WO | WO 2008/155506 A1 | 12/2008 |
| WO | WO 2009/047444 A1 | 4/2009 |
| WO | WO 2010/055273 A1 | 5/2010 |
| WO | WO 2010/089512 A1 | 8/2010 |
| WO | WO 2013/011226 A1 | 1/2013 |

OTHER PUBLICATIONS

Umicore (website) Oct. 2005.*
International Search Report (PCT/ISA/210) mailed on Sep. 17, 2014, by the European Patent Office as the International Searching Authority for International Application No. PCT/FR2014/050247.
Written Opinion (PCT/ISA/237) mailed on Sep. 17, 2014, by the European Patent Office as the International Searching Authority for International Application No. PCT/FR2014/050247.

* cited by examiner

*Primary Examiner* — Gregory Listvoyb
(74) *Attorney, Agent, or Firm* — Buchanan Ingersoll & Rooney P.C.

(57) ABSTRACT

A method for the combined synthesis of a mono-unsaturated nitrile-ester(acid) and of a bi-functional carbonyl compound, wherein it includes a step including the cross metathesis mc1 of an unsaturated fatty acid/ester compound with an unsaturated nitrile compound, in which mc1 is performed with partial conversion such as to obtain and recover, separately, at least the following products: a mono-unsaturated nitrile-ester/acid and a symmetrical compound, diester or diacid respectively including a double bond located in the middle of the molecular chain of compound, and subsequently a step including the oxidation cleavage cp2 of the double bond of compound, such as to form a single type of carbonyl compound having formula $R_2\text{-}(CH_2)_n\text{-}COR'$, in which R' is H or OH, depending on the operating conditions selected for the oxidation cleavage cp2. Also, the production of monomers for the polymer industry.

27 Claims, 2 Drawing Sheets

COMBINED SYNTHESIS OF A NITRILE-ESTER/ACID AND OF A DIESTER/DIACID

The work which led to this invention received financial support from the European Union in the context of Framework Program 7 (FP7/2007-2013) under project No. 241718 EUROBIOREF.

FIELD OF THE INVENTION

The present invention relates to a process for the conjugate synthesis of a nitrile acid/ester and of a diacid/diester (or derivatives thereof) in high purity from an unsaturated fatty acid/ester of natural origin, said process comprising at least one step of cross metathesis and a step of oxidative cleavage. The invention especially relates to the synthesis both of ω-amino acid/ester and of diacid/diester, which are two products of interest for the synthesis of monomers and polymers, such as specialty polyamides (PA).

TECHNICAL BACKGROUND

The polyamide industry uses a whole range of monomers, mainly lactams, ω-amino acids and "diamine-diacid" couples, denoted by the number of carbons per amide contained in the repeating unit of the polyamide. Mention may be made, for example, of the following polyamides: PA 6, PA 6.6, PA 6.10, PA 7, PA 8, PA 9, PA 11, PA 12, PA 13.

These monomers are manufactured, for example, via a chemical synthesis route especially using as starting material C2 to C4 olefins, cycloalkanes or benzene, but also castor oil (PA 11), erucic oil or lesquerolic oil (PA 13).

Current developments in environmental matters are leading, in the fields of energy and chemistry, to the exploitation of natural raw materials originating from a renewable source being favored. This is why certain studies have been undertaken in order industrially to develop processes using fatty acids/esters as starting material for manufacturing these monomers.

This type of approach has few industrial examples. One of the rare examples of an industrial process using a fatty acid as starting material is that for the manufacture, from ricinoleic acid extracted from castor oil, of 11-aminoundecanoic acid, which is the basis for the synthesis of polyamide 11 having the brand name Rilsan®. This process is described in the book *Les Procédés de Pétrochimie* by A. Chauvel et al. published by Editions TECHNIP (1986). 11-Aminoundecanoic acid is obtained in several steps: methanolysis of castor oil, pyrolysis of the methyl ricinoleate to obtain methyl undecylenate, which is hydrolyzed, and the acid formed is subjected to a hydrobromination to give the ω-bromo acid, which passes via amination to 11-aminoundecanoic acid.

The main research studies have related to the synthesis of 9-aminononanoic acid, which is a precursor of Nylon 9, from oleic acid of natural origin.

As regards this particular monomer, mention may be made of the publication *n-Nylons, Their Synthesis, Structure and Properties*—1997, published by J. Wiley and Sons, chapter 2.9 of which (pages 381 to 389) is devoted to polyamide 9. This article summarizes the achievements and studies performed on the subject. Mention is made, on page 381, of the process developed by the former Soviet Union which led to the marketing of Pelargon®. Mention is also made therein, on page 384, of a process developed in Japan using oleic acid originating from soybean oil as starting material. The corresponding description makes reference to the book by A. Ravve *Organic Chemistry of Macromolecules* (1967) Marcel Dekker, Inc., part 15 of which is devoted to polyamides and mentions on page 279 the existence of such a process.

For a full picture of the prior art, mention should be made of the numerous articles published by E. H. Pryde et al. between 1962 and 1975 in—Journal of the American Oil Chemists Society—*Aldehydic Materials by the Ozonization of Vegetable Oils*, Vol. 39 pages 496-500; *Pilot Run, Plant Design and Cost Analysis for Reductive Ozonolysis of Methyl Soyate* Vol. 49 pages 643-648 and R. B. Perkins et al. *Nylon-9 from Unsaturated Fatty Derivatives: Preparation and Characterization* JAOCS, Vol. 52 pages 473-477. It should be noted that the first of these articles also makes reference on page 498 to prior studies performed by Japanese: H. Otsuki and H. Funahashi.

To summarize this prior art directed toward this type of synthesis of PA 9 from plant oils, the following simplified reaction mechanism applied to the maleic ester, extracted from the oils by methanolysis, may be described:

Reductive Ozonolysis:

Reductive Amination:

$OHC-(CH_2)_7-COOCH_3+(NH_3,H_2) \rightarrow H_2N-(CH_2)_8-COOCH_3+H_2O$ followed by hydrolysis leading to the amino acid.

This route, which is very appealing as regards the reaction, nevertheless has a large economic drawback consisting of the production during the first step of pelargonic aldehyde, which is very difficult to upgrade, including in the polyamide industry.

Patent GB 741 739 describes, for its part, the synthesis of this same acid from oleic acid, but using the oleonitrile route. A similar route is mentioned in the article by R. B. Perkins et al. mentioned above, page 475.

The simplified reaction scheme of this process is as follows.

The synthesis leads to pelargonic acid (or nonanoic acid) $H_3C-(CH_2)_7-COOH$ as by-product.

The Applicant has, for its part, developed processes for manufacturing such ω-amino acid monomers which especially use metathesis reactions. Mention may be made in this respect of patent applications WO 08/104 722, WO 10/055 273 and WO 10/089 512, which describe processes in which the terminal amine function of the ω-amino acid results from the hydrogenation of a nitrile function, introduced either by cross metathesis with acrylonitrile (WO 08/104 722) or by ammoniation of the acid function (WO 10/055 273 and WO 10/089 512) in the context of a process proceeding via an ω-unsaturated nitrile or a monounsaturated dinitrile.

The diacids are, for their part, obtained industrially according to various methods, but which all have certain drawbacks. A wide panorama of these methods is developed in Kirk-Othmer's encyclopedia, 4th Edition, vol. A8, pages 118-136. Methods by degradation, such as ozonolysis or oxidation, of plant unsaturated fatty acids may be distinguished therein.

The ozonolysis of oleic acid, petroselinic acid and erucic acid makes it possible to produce, respectively, diacids containing 9, 6 and 13 carbon atoms.

Another example is the cleavage of ricinoleic acid via the action of sodium hydroxide at a temperature above 180° C. This method used industrially makes it possible to obtain the diacid containing 10 carbon atoms. The same method applied to lesquerolic acid leads to the formation of a diacid containing 12 carbon atoms.

This method has the advantage of using renewable starting materials, but is limited essentially to the manufacture of the C10 diacid, since lesquerolic acid is still not widespread, and this method is therefore sparingly used.

It is also possible to obtain diacids from molecules of smaller sizes by using techniques that are variants of carbonylation.

Finally, mention may be made of the bacterial fermentation of paraffins, which is a well-known method that makes it possible to obtain numerous diacids of variable chain length. However, this method does not make it possible to obtain diacids with a chain length greater than 16 carbon atoms, since the melting point of the paraffins is then too high to allow them to be transformed. Another important drawback is that bacteria consume some of the paraffins to ensure their growth, leading to low yields and to the need to purify the products.

The ozonolysis of erucic acid and oleic acid is used industrially for the production of diacids containing 13 and 9 carbon atoms, respectively. This technique has several drawbacks. Specifically, in the case of production of the diacid containing 9 carbon atoms, the starting material is oleic acid. This is present in nature as a mixture with stearic acid (acid of the same chain length but saturated). Stearic acid cannot react during the ozonolysis. However, it has a boiling point close to that of the diacid containing 9 carbon atoms, which complicates its separation. It is thus necessary either to use a very pure oleic acid (which is consequently more expensive) or to use efficient but expensive separation techniques downstream of the oxidative cleavage process to isolate the diacid. Moreover, these oxidative cleavage processes generate as coproduct pelargonic acid—a saturated linear acid containing 9 carbon atoms—which is aimed at a very different market (lubricants, herbicides, etc.) from that of the polymers, whereas the diacids are aimed at the markets of polyamides, polyesters and solvents (esters). In this type of process, products and coproducts have different growth markets. Further, as one of the products has a low growth value or even a degrowth value, the economic value of the process and thus that of the other product is largely reduced. It is thus advantageous, when a product is obtained with a coproduct, to find applications that address the same markets.

The Applicant has, for its part, launched studies in this field, which especially use the metathesis reactions in the context of a multi-reaction process.

Patent WO 08/155 506 describes a process that consists, in a first step, in transforming by pyrolysis or ethenolysis the unsaturated fatty ester into ω-unsaturated fatty ester and then, in a second step, in subjecting the product thus obtained to a metathesis reaction, either homometathesis to obtain a compound of formula ROOC—$(CH_2)_m$—CH=CH—$(CH_2)_m$—COOR, or cross metathesis with a compound of formula $R_2$OOC—$(CH_2)_r$—CH=CH—$R_3$ to obtain an unsaturated compound of formula ROOC—$(CH_2)_m$—CH=CH—$(CH_2)_r$—COOR$_2$, which will be transformed by hydrogenation into saturated compounds.

Patent WO 09/047 444 describes a process for synthesizing diacids or diesters from monounsaturated long-chain natural fatty esters, which consists, in a first step, in oxidizing by fermentation the natural fatty ester to a monounsaturated carboxylic diester and then, in a second step, in subjecting the product from the first step to cross metathesis with a compound of formula $R_2$OOC—$(CH_2)_x$—CH=CH—$R_3$ to obtain an unsaturated compound of formula ROOC—$(CH_2)_q$—CH=CH—$(CH_2)_x$—COOR$_2$, which, by hydrogenation, can lead to the saturated compound.

In a known manner, cross metathesis consists in reacting, in the presence of a catalyst, two unsaturated molecules according to the following schematic reaction process:

$A_1A_2$-C=C-$B_1B_2$+$D_1D_2$-C=C-$E_1E_2$ ⇔

$A_1A_2$-C=C-$D_1D_2$+$A_1A_2$-C=C-$E_1E_2$+$B_1B_2$-C=C-$D_1D_2$+$B_1B_2$-C=C-$E_1E_2$

Such an equilibrated reaction naturally poses problems with a view to an industrial use. The presence of four reaction products when the two reaction compounds are added, which, by hypothesis, have not completely reacted, contributes toward forming a complex mixture.

A person skilled in the art is always seeking to influence the composition of the resulting reaction mixture by carefully choosing the respective amounts of the two reagents and also the structure of the reagent $D_1D_2$-C=C-$E_1E_2$ so that the products formed are readily separable from the medium, and especially separable in gaseous form, which also has the advantage of shifting the reaction equilibrium and thus increasing the amounts of reaction products. The difficulty lies in selecting reagents which do not interfere with the products, and which do not generate coproducts that are difficult to separate from the reaction products.

It should be noted, however, that the reaction is performed in the presence of a catalyst that is also active for homometathesis reactions. This means that, besides the reactions mentioned above, the reaction below also takes place:

$A_1A_2$-C=C-$B_1B_2$+$D_1D_2$-C=C-$E_1E_2$ ⇔

$A_1A_2$-C=C-$A_1A_2$+$B_1B_2$-C=C-$B_1B_2$+$D_1D_2$-C=C-$D_1D_2$+$E_1E_2$-C=C-$E_1E_2$

This implies that during a cross metathesis, the operator's reaction medium comprises ten potential products. To limit the number of potential metathesis products, it is possible in certain cases to limit the formation of certain by-products and/or to limit the chemical feasibility of certain reactions intervening during the metathesis. This may be done especially by choice of the coreagent and/or by a separation of certain compounds gradually as they are formed. For example, by selecting compounds containing a double bond that is terminal or close to the end of the chain, the reaction coproducts will be light (gaseous) olefins which will be spontaneously removed from the liquid reaction medium.

Added to these obstacles inherent in the actual reaction is a difficulty associated with the catalyst, which, besides its activity in metathesis, is also active in isomerization. It has been observed, in certain cases, that this isomerizing activity of the catalyst increases when its metathesis activity decreases. The metathesis catalyst deactivated for the metathesis reaction appears to become transformed into a species that is active for catalyzing isomerization reactions. Under these conditions, the catalyst "in the depletion phase" in the presence of the long-chained olefins of the charge or of the products brings about a shift of the double bond of the reagent and/or fatty acid product. This leads to mixtures of isomers and brings about the formation of a mixture of products having different chain lengths. Since these chain lengths are, however, very similar, their respective separations are particularly difficult.

When cross metathesis is used for the purpose of synthesizing a target product, for example $A_1A_2$–C=C–$D_1D_2$ in the preceding equation, this product will therefore be accompanied, where appropriate, by the other three compounds of the cross metathesis and also by certain compounds derived from homometathesis, which is a reaction that automatically accompanies the main reaction, but also mixtures of isomers of these compounds.

The aim of the present invention is to manufacture "pure" products rather than mixtures, and the aim is thus to provide a process in which the yield of target product is maximized and in which the coproduct(s) synthesized have a substantial added value and a sufficient degree of purity without it being necessary to apply sophisticated and thus expensive purification techniques. An aim of the present invention is also to provide a process in which the product and coproduct preferably address the same final market.

The Applicant has now found such a process for overcoming the preceding drawbacks and for producing both an ω-amino acid as main product and a pure long-chain diester/diacid as coproduct, or difunctional derivatives thereof such as acid (ester)-alcohols, all making it possible directly to manufacture monomers for the polymer industry. The process of the invention thus makes it possible to provide on the same site two starting materials that can be used for the same purpose, namely the manufacture of polymers, and better still in the same type of polymerization process.

Without wishing to be bound by any theory, the Applicant thinks that the isomerizing activity of the metathesis catalyst decreases during the homometathesis reaction of the fatty acid if the homometathesis reaction is performed concomitantly with a cross metathesis in the presence of an unsaturated nitrile coreagent, which makes it possible to achieve the surprising result obtained by the process of the invention.

DESCRIPTION OF EMBODIMENTS OF THE INVENTION

One subject of the invention is thus a process for the conjugate synthesis of a monounsaturated nitrile ester (acid) (III) and of a symmetrical or unsymmetrical difunctional carbonyl compound (V), of formula $R_2$—$(CH_2)_n$-COR' in which R' is H or OH, from an (the same) unsaturated fatty compound (I) comprising at least one ester or acid function, respectively, of formula $$R_1\text{—CH=CH—}[(CH_2)_q\text{—CH=CH}]_p\text{—}(CH_2)_n\text{—}R_2 \quad (I)$$

in which:
$R_1$ is H or an alkyl radical comprising from 1 to 4 carbon atoms, $R_2$ is an ester or acid function and n, p and q are integers such that 3≤n≤13; 0≤p≤2; 0≤q≤1
characterized in that it comprises:
a step of cross metathesis cm1 of compound (I) with an unsaturated nitrile compound (II) chosen from acrylonitrile, fumaronitrile, 2-butenenitrile, 1-butenenitrile, 2-pentenenitrile, 3-pentenenitrile, 4-pentenenitrile and 1-pentenenitrile,
in which cm1 is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound (IV) of formula $R_2$—$(CH_2)_n$—HC=CH—$(CH_2)_n$—$R_2$ resulting from the homometathesis of compound (I),
and then
a step of oxidative cleavage cl2 of the double bond respectively of the diester or diacid compound (IV), so as to form a single type of carbonyl compound (V) of formula $R_2$—$(CH_2)_n$—COR' in which R' is H or OH, depending on the operating conditions chosen for the oxidative cleavage cl2.

For the purposes of the invention, the term "conjugate synthesis" of two products means the simultaneous synthesis, during the process of the invention, of two target products occasionally referred to here in as the product and the coproduct, namely compound III, on the one hand, and compound V, on the other hand.

For the purposes of the invention:
the term "pure" product or coproduct means a product containing few impurities, typically less than 15% by weight, preferably less than 10%, preferably less than 5%, more preferably less than 2% or better still less than 1% by weight, relative to the weight of product or coproduct;
the term "long-chain" product or coproduct means herein a product whose main chain comprises at least 8 carbon atoms, preferably from 8 to 20 carbons, preferably from 9 to 18 carbons, preferably from 9 to 14 carbons, preferably 9, 10 or 13 carbon atoms for the final diacid/diester, preferably 11 or 12 or 13 carbon atoms for the final acid/ester-nitrile or the final amino acid/amino ester.

For the purposes of the invention, the term "fatty" compound means a compound which preferably comprises from 10 to 24 carbon atoms, preferably from 14 to 24 carbon atoms per molecule.

The unsaturated fatty compound (I) of formula $R_1$—CH=CH—$[(CH_2)_q$—CH=CH$]_p$—$(CH_2)_n$—$R_2$ is advantageously chosen from fatty acids or fatty acid esters, these esters possibly being esters of monoalcohol, of diol or of triol, including mono-, di- and triglycerides, of plant or animal origin, including those derived from natural algae.

Compound I comprises at least one unsaturation, i.e. a C=C double bond. The unsaturation is located in position x relative to the acid or ester group, this position conventionally being referred to as "delta x". This makes it possible to determine the formula of the final ω-amino acid.

Examples of fatty acids that may be mentioned include C10 acids, obtusilic acid (cis-4-decenoic acid) and caproleic acid (9-decenoic acid), C12 acids, lauroleic acid (cis-5-dodecenoic acid) and linderic acid (cis-4-dodecenoic acid), C14 acids, myristoleic acid (cis-9-tetradecenoic acid), physeteric acid (cis-5-tetradecenoic acid) and tsuzuic acid (cis-4-tetradecenoic acid), C16 acids, palmitoleic acid (cis-9-hexadecenoic acid), C18 acids, oleic acid (cis-9-octadecenoic acid), elaidic acid (trans-9-oxodecenoic acid), petroselinic acid (cis-6-octadecenoic acid), vaccenic acid (cis-11-octadecenoic acid) and ricinoleic acid (12-hydroxy-cis-9-octadecenoic acid), C20 acids, gadoleic acid (cis-9-eicosenoic acid), gondoic acid (cis-11-eicosenoic acid), cis- 5-eicosenoic acid and lesquerolic acid (14-hydroxy-cis-11-eicosenoic acid), C22 acids, cetoleic acid (cis-11-docosenoic acid) and erucic acid (cis-13-docosenoic acid), and also the polyunsaturated acids linoleic acid and linolenic acid.

These various acids are derived from plant oils extracted from various oleagineous plants, such as sunflower, rape, castor oil plant, Lesquerella, olive, soya, palm tree, avocado, sea buckthorn, coriander, celery, dill, carrot, fennel, Limnanthes alba (meadowfoam), safflower, camelina or Jatropha. They are also derived from the terrestrial or marine animal world and, in this case, either in the form of fish, mammals or algae. They are generally fats originating from ruminants, fish such as cod, or marine mammals such as whales or dolphins.

For technical reasons of performing the metathesis reaction, it is often preferable to modify this fatty ester/acid by subjecting it to a prior reaction comprising an ethenolysis, butenolysis or propenolysis or thermal cracking (pyrolysis) leading to a fatty acid (ester) of formulae such as $CH_2=CH-(CH_2)_n-R_2$, $CH_3-CH=CH-(CH_2)_n-R_2$ or $CH_3-CH_2-CH=CH-(CH_2)_n-R_2$.

Even more preferably, compound I is a fatty acid or ester of formula $CH_2=CH-(CH_2)_n-COOR_3$ in which
$R_3$ is H or an alkyl radical comprising from 1 to 11 carbon atoms, and
n is an integer in the range from 3 to 13.

The unsaturated nitrile compound (II) is advantageously chosen from: acrylonitrile, fumaronitrile, 2-butenenitrile, 1-butenenitrile, 2-pentenenitrile, 3-pentenenitrile, 4-pentenenitrile and 1-pentenenitrile, and mixtures thereof.

The cross metathesis step is preferably performed with acrylonitrile for the nitrile compound (II). The reason for this is that acrylonitrile is widely available, inexpensive and in particular is the only nitrile that can give 11-aminoundecanoic acid from methyl decenoate. Another advantage is that the reaction coproduct is the lightest possible olefin: ethylene.

The cross metathesis step according to the process of the invention is performed to partial conversion so as to obtain and to recover separately compounds III and IV.

Advantageously, the cross metathesis step cm1 is performed to a degree of conversion in the range from 30% to 99%, preferably from 30% to 90%, preferably from 40% to 90%. The degree of conversion is governed by the operating conditions and especially the duration of the reaction and the means used for extracting the gaseous compound formed during the metathesis reaction. Furthermore, it is advantageous to limit this degree of conversion so as to preserve the performance of the catalyst.

Advantageously, the process of the invention also comprises a step of hydrogenation of the monounsaturated ester/acid nitrile (III) obtained to form a saturated α,ω-amino ester/acid.

Advantageously, the process also comprises, in the case where (IV) is a diester, an optional intermediate step of hydrolysis between cm1 and cl2 to obtain a diacid compound (IV).

The metathesis reaction is performed in the presence of at least one metathesis catalyst. These catalysts are well known and an entire range of them exists. Mention may, for example, be made of the tungsten complexes developed by Schrock et al (*J. Am. Chem. Soc.* 108:2771, 1986) or Basset et al. (*Angew. Chem., Ed. Engl.* 31:628, 1992). More recently, catalysts termed Grubbs catalysts have emerged (see Grubbs et al., *Angew. Chem., Ed. Engl.* 34:2039, 1995 and *Organic Letters* 1:953, 1999) which are ruthenium-benzylidene complexes operating in homogeneous catalysis.

Other studies have been carried out in order to produce immobilized catalysts, i.e. catalysts of which the active ingredient is that of the homogeneous catalyst, in particular ruthenium-carbene complexes immobilized on an inactive support.

The process according to the invention advantageously uses at least one metathesis catalyst of ruthenium-carbene type. Said ruthenium-carbene catalyst is preferably chosen from charged or uncharged catalysts of general formula:

$(X_1)_a(X_2)_b\text{Ru}(\text{carbene C})(L_1)_c(L_2)_d(L_3)_e$ in which:

a, b, c, d and e are integers, which may be identical or different, with a and b equal to 0, 1 or 2; c, d and e equal to 0, 1, 2, 3 or 4;

$X_1$ and $X_2$, which may be identical or different, each represent a charged or uncharged and monochelating or polychelating ligand; by way of examples, mention may be made of halides, sulfate, carbonate, carboxylates, alkoxides, phenoxides, amides, tosylate, hexafluorophosphate, tetrafluoroborate, bis(triflyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

The carbene C is represented by the general formula: $CR_1R_2$ for which $R_1$ and $R_2$ are groups which may be identical or different, such as hydrogen or any other functionalized or non-functionalized hydrocarbon-based group of saturated, unsaturated, cyclic, aromatic, branched and/or linear type. By way of examples, mention may be made of ruthenium alkylidene, benzylidene, benzylidene ether or cumylene complexes, such as vinylidenes $Ru=C=CHR$ or allenylidenes $Ru=C=C=CR_1R_2$ or indenylidenes.

A functional group (making it possible to improve the retention of the ruthenium complex in an ionic liquid) can be grafted onto at least one of the ligands $X_1$, $X_2$, $L_1$, $L_2$, or onto the carbene C. This functional group may be charged or uncharged, such as preferably an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The metathesis catalyst can optionally be rendered heterogeneous on a support in order to facilitate the recovery/recycling thereof.

The cross metathesis catalysts of the process of the invention are preferably ruthenium carbenes described, for example, in *Aldrichimica Acta*, vol. 40, No. 2, 2007, pp. 45-52.

Examples of such catalysts are Grubbs catalysts, Hoveyda-Grubbs catalysts, Piers-Grubbs catalysts, and other metathesis catalysts of the same type, whether they are "1st-generation", "2nd-generation" or "3rd-generation" catalysts.

Grubbs catalysts are based on a ruthenium atom surrounded by 5 ligands:
- 2 anionic ligands, such as halides;
- 2 electron-donating ligands, such as trialkyl phosphines, or saturated N-heterocyclic carbenes (called NHC ligands);
- an alkylidene group, such as substituted or unsubstituted methylene groups $=CR_2$.

These metathesis catalysts are classified into two categories, depending on the nature of their electron-donating ligands L:
- those which contain two phosphine ligands (and no saturated NHC ligand), developed first, are 1st-generation catalysts;
- those which contain a saturated NHC ligand (a heterocyclic carbene) are 2nd-generation catalysts.

A type of catalyst known as a "Hoveyda-Grubbs" catalyst contains, among the electron-donating ligands, a benzylidene-ether chelating ligand, and either a phosphine (1st generation) or a saturated NHC ligand (2nd generation), usually substituted with phenyls generally substituted with mesityl (Mes) groups or else with isopropyl (iPr) groups.

Another type of catalyst termed "Piers-Grubbs" catalyst forms a four-ligand cationic complex which does not require dissociation of a ligand before the reaction.

Other types of catalysts are the "Umicore", "Zanan" and "Greta" catalysts.

Generally, the choice of the catalyst depends on the reaction under consideration.

According to an advantageous embodiment, the catalyst is free of phosphine.

Preferred catalysts are the catalysts which follow:

(1) The catalyst denoted "Hoveyda-Grubbs 2", having the following formula:

(2) The catalyst denoted "M51", having the following formula:

(3) The catalyst denoted "M71-SIPr", having the following formula:

(4) The catalyst denoted "M71-SIMes", having the following formula:

(4) The catalyst denoted "M72-SIPr", having the following formula:

(5) The catalyst denoted "M73-SIPr", having the following formula:

(6) The catalyst denoted "M74-SIPr", having the following formula:

(7) The catalyst denoted "Nitro-Grela-SIMes", having the following formula:

(8) The catalyst denoted "Nitro-Grela-SIPr", having the following formula:

(9) The catalyst denoted "Apeiron AS2034", having the following formula:

(10) The catalyst denoted "Zannan 44-0082 (Strem)", having the following formula:

(11) The catalyst denoted "M831-SIPr", having the following formula:

(12) The catalyst denoted "M832-SIPr", having the following formula:

(13) The catalyst denoted "M853-SIPr", having the following formula:

(14) The catalyst denoted "M863-SIPr", having the following formula:

(15) The catalyst denoted "Materia C711", having the following formula:

The metathesis reaction is preferably performed in liquid medium under the following operating conditions.

The temperature is generally in the range from 20 to 160° C. and preferably in the range from 20 to 120° C.

The pressure is generally in the range from 1 to 30 bar. The reaction will preferably be performed at low pressure in the range from 1 to 10 bar and more preferably at atmospheric pressure when the boiling point of the reagents used makes it possible. Specifically, if a mild evolution of olefin, ethylene or the like, is always intended, it is advantageous to work at low pressure, preferably atmospheric pressure. For example, a compound such as C3 acrylonitrile whose boiling point is of the order of 80° C. makes it possible to work at atmospheric pressure.

The reaction may be performed without solvent or in the presence of at least one solvent, such as toluene, xylenes or dichloromethane, for example. The reaction is preferably performed without solvent.

The symmetrical unsaturated diester or diacid compound (IV) is subjected in the process of the invention to oxidative cleavage or cleavage by oxidation of the double bond, which leads to the formation of a single type of carbonyl compound V.

The oxidative cleavage reaction is a reaction that is well known. The process of the invention uses in step cl2 one or more types of oxidative cleavage reactions, such as those described below.

According to a first embodiment, the cleavage is performed using a strong oxidizing agent such as $KMnO_4$ in concentrated form and with heating (temperature in the range from 20 to 150° C.), as described, for example, in *Organic Chemistry* by L. G. Wade Jr. 5$^{th}$ Edition Chapter 8 Reactions of Alkenes.

According to a second embodiment, the cleavage is performed using a strong oxidizing agent such as ammonium chlorochromate. The article by G. S. Zhang et al. in *Chinese Chemical Letters*, vol. 5, No. 2, pp. 105-108, 1994, describes oxidative cleavage using the diol corresponding to oleic acid (see entry 29 of the table); this oxidative cleavage is performed using ammonium chlorochromate as oxidizing agent. As regards the diol, it is obtained by epoxidation of oleic acid followed by hydrolysis of the epoxy bridge.

According to a third embodiment, the cleavage is performed by irradiation. The article by F. Drawert et al. in Chem. Mikrobiol. Technol. Lebensm. 1, 158-159 (1972) describes an oxidative cleavage route by irradiation of sunflower oil.

Usually, these cleavages with a strong oxidizing agent lead to the formation of compounds of acid type.

According to another preferred embodiment, the oxidative cleavage cl2 is performed using aqueous hydrogen peroxide solution and/or ozone as oxidizing agent.

These routes are especially presented in patent GB 743 491 which illustrates the mechanisms of the reactions involving aqueous hydrogen peroxide solution and/or ozone, with the formation of ozonides on the double bond cleavage. U.S. Pat. No. 2,813,113 describes an ozonolysis process for oxidizing a fatty acid such as oleic acid, which consists in a first step in treating the acid with oxygen combined with ozone to form ozonides, and then in a second step in oxidizing these ozonides with oxygen. Numerous studies have been performed regarding the use of ozone as an oxidizing agent. The oxidative cleavage of oleic acid to pelargonic acid and azelaic acid is the most important industrial application of ozonolysis.

The final product obtained depends on the conditions under which the oxidation reaction by ozonolysis or with aqueous hydrogen peroxide solution is performed. In case of an ozonolysis performed in an oxidizing medium (in the presence of oxygen), the oxidation process continues up to the formation of acid functions; this is then referred to as oxidative ozonolysis. On the other hand, if the oxidation is performed under reductive conditions, by decomposition of the ozonide in the presence of hydrogen, for example, or in the presence of compounds that block the oxidation process, the oxidation stops at the aldehyde stage; this is then referred to as reductive ozonolysis.

In the case of a cleavage by oxidation with aqueous hydrogen peroxide solution, the operating conditions may be adapted either to touch the acid functions by doping the reaction with $O_2$, which, in this case also, is an oxidative cleavage, or to block the reaction at the aldehyde stage, and this will be referred to as cleavage by reductive oxidation. To facilitate the terminology, use will often be made of the terms "oxidative cleavage" for that leading to the acid and "reductive cleavage" for that leading to the aldehyde.

Depending on the industrial needs, the conditions of the cleavage are adapted to obtain either the ester/acid-aldehyde $R_2$—$(CH_2)_n$—CHO or the diacid or the ester-acid $R_2$—$(CH_2)_n$—COOH, leading by hydrolysis to the diacid.

In one variant of the process using reductive ozonolysis, by decomposition of the ozonide in the presence of $H_2$, for example, or cleavage with $H_2O_2$ under "reductive" conditions, the reaction may be continued with a reduction of the aldehyde to obtain an alcohol function. This route makes it possible to obtain an ester/acid-alcohol $R_2$—$(CH_2)_n$—$CH_2OH$, which is a monomer of long-chain polyesters. This approach applies equally and is even particularly pertinent in the case of reductive ozonolysis, where the intermediate ozonide is decomposed by hydrogen in the presence of a catalyst (for example Pt) to form the aldehyde, and it suffices to continue the reduction of the aldehyde to an alcohol in order to obtain the desired monomer.

The oxidative cleavage step cl2 is optionally followed by at least one optional step chosen from:
  oxidation of the aldehyde in the presence of dioxygen to transform it into acid;
  hydrolysis of the ester function to form a diacid of formula HOOC—$(CH_2)_n$—COOH;

reductive amination of the aldehyde function to an amino ester/acid;
  hydrogenation of the aldehyde-ester/acid to alcohol-ester or alcohol-acid, respectively, which may be used in the synthesis of polyesters;
  ammoniation of the acid-ester or of the diacid for its conversion into dinitrile and then optionally hydrogenation to diamine;
  esterification and/or transesterification of the acid-ester or of the diacid;
  and mixtures of these steps.

A subject of the present invention is also a process for manufacturing intermediate compound(s) according to the invention, characterized in that it comprises:
  starting with the same unsaturated fatty compound (I) comprising, respectively, at least one ester or acid function, of formula:

$R_1$—CH=CH—[$(CH_2)_q$—CH=CH]$_p$—$(CH_2)_n$—$R_2$ (I)

in which $R_1$ is H or an alkyl radical comprising from 1 to 4 carbon atoms, $R_2$ is an ester or acid function and n, p and q are integers such that $3 \le n \le 13$; $0 \le p \le 3$; $0 \le q \le 1$,
  a step of cross metathesis cm1 of compound (I) with an unsaturated nitrile compound (II) chosen from: acrylonitrile, fumaronitrile, 2-butenenitrile, 1-butenenitrile, 2-pentenenitrile, 3-pentenenitrile, 4-pentenenitrile and 1-pentenenitrile, in which cm1 is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound (IV) of formula $R_2$—$(CH_2)_n$—HC=CH—$(CH_2)_n$—$R_2$ resulting from the homometathesis of compound (I).

Advantageously, the process according to the invention also comprises the hydrogenation of at least part of the symmetrical compound (IV) leading to the corresponding saturated compound (IVs) of formula $R_2$—$(CH_2)_n$—$CH_2$—$CH_2$—$(CH_2)_n$—$R_2$. Advantageously, the synthetic process according to the invention also comprises a step of hydrogenation of the monounsaturated ester/acid nitrile (III) obtained to form a saturated α,ω-amino ester/acid.

A subject of the present invention is also a process for synthesizing polymer, especially polyamide, by polymerization using at least one monomer manufactured according to the process of the invention, especially comprising at least one ω-amino acid, ω-amino ester, diacid and/or diester, obtained according to the process of the invention. A subject of the present invention is also a polymer, especially a polyamide, characterized in that it comprises at least one monomer, especially comprising at least one ω-amino acid, ω-amino ester, diacid and/or diester, manufactured according to the process of the invention.

Preferably, the polymer, especially polyamide, according to the invention is characterized in that it comprises at least one of the following polyamide monomers: 4.6, 4.T, 5.6, 5.9, 5.10, 5.12, 5.13, 5.14, 5.16, 5.18, 5.36, 6, 6.6, 6.9, 6.10, 6.12, 6.13, 6.14, 6.16, 6.18, 6.36, 6.T, 9, 10.6, 10.9, 10.10, 10.12, 10.13, 10.14, 10.16, 10.18, 10.36, 10.T, 11, 12, 12.6, 12.9, 12.10, 12.12, 12.13, 12.14, 12.16, 12.18, 12.36, 12.T, and mixtures thereof; and is preferably chosen from PA 11, PA 12, PA 10.10, PA 6, PA 6.10, PA 6.12, PA 10.12, PA 6.14 and/or PA 6.6/6, PA 11/10.10, and mixtures thereof.

EXAMPLES

The following examples illustrate the invention without limiting it.

Example 1

Metathesis of Methyl 9-decenoate with Acrylonitrile

The reaction scheme for the reaction is as follows.

The catalyst used for this metathesis reaction is the catalyst M71-SiPr, supplied by the company Umicore, of formula (3):

15 g of methyl 9-decenoate (81.4 mmol) prepared in accordance with Example 1 of document US 2011/0 113 679, previously passed over an alumina column, 2.15 g of acrylonitrile (40.7 mmol) and 150 g of toluene dried on molecular sieves are charged to a 250 ml glass reactor equipped with a condenser and purged with nitrogen. The mixture is heated to 110° C. and 2.6 g of acrylonitrile (49 mmol) and 2 mg of M71-SiPr catalyst ($2.44 \times 10^{-6}$ mol) dissolved in 5 g of toluene are added via syringes mounted on a syringe driver, over a period of 2 h.

The reaction mixture obtained is analyzed by gas chromatography. The conversion of the methyl 9-decenoate is 89%. The selectivity toward $C_{11}$ unsaturated nitrile-ester is 81% and the selectivity toward $C_{18}$ unsaturated diester is 19%.

Figure 1:
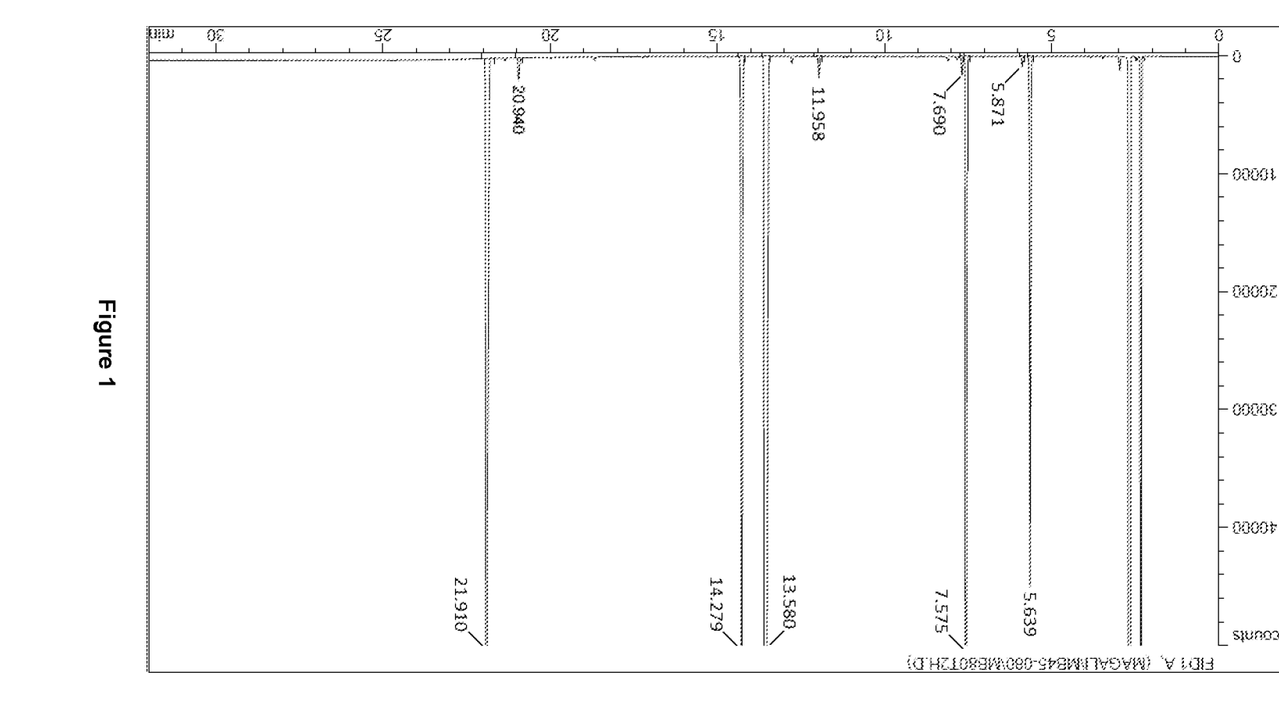
FIG. 1 is a chromatograph illustrating products of the reaction of Example 1.

FIG. 1 is a chromatograph showing, next to the peaks corresponding to the nitrile esters, main products of the reaction of Example 1, the characteristic peak of methyl 9-octadecenedioate (peak at 21.9 min) accompanied by a peak of very small amplitude at 20.9, corresponding to another diester. The relative selectivity (methyl 9-octadecenedioate/total diesters) for the homometathesis reaction is greater than 98.5%, calculated on the basis of a surface area ratio of the peaks of the chromatograph.

Example 2

Hydrolysis of the Unsaturated $C_{18}$ Diester

The reaction mixture obtained in Example 1 is evaporated and the $C_{11}$ nitrile ester is then distilled under vacuum (boiling point=121-123° C. at 0.8 mbar).

The distillation tail fraction containing the unsaturated C18 diester is recovered. 30 g of diester (88 mmol) and 200 g of water are placed in a reactor. The mixture is heated to 80° C. and 88 ml of 1M sodium hydroxide (88 mmol) are added. The mixture is left to react for 1 hour at 80° C. The temperature is lowered to 50° C. and aqueous 1M HCl solution is added until a pH of 2 is obtained. The reaction mixture is filtered and the precipitate is dried under vacuum. 9-Octadecenedioic acid is thus obtained.

Example 3

Oxidative Cleavage of the Unsaturated $C_{18}$ Diacid

34.9 g of nonanoic acid (Aldrich, 97%), 12.8 g of 9-octadecenedioic acid and 2.5 g of tungstic acid ($H_2WO_4$; Merck 98%) are introduced into a 100 ml jacketed reactor comprising a mechanical stirrer and a condenser, and then stirred and heated at 78° C., said temperature being maintained by circulation of thermostatic water/glycol. 11.1 g of aqueous hydrogen peroxide solution ($H_2O_2$ concentration equal to 70.0% by weight) are added dropwise using a peristaltic pump over a duration of 6 hours. After the first hour, a stream of air of 400 ml/min is injected into the reaction mixture using a Teflon tube. The reaction is stopped after 24 hours.

At the end of the reaction, the organic phase is washed several times with demineralized water until the hydrogen peroxide has disappeared from the washing water, and it is then dried under vacuum and analyzed by GC. The conversion is greater than 95%. The yield of azelaic acid ($C_9$ diacid) is 33%.

Example 4

Metathesis of Methyl Undecenoate with Acrylonitrile

The reaction scheme is as follows.

-continued 15 g of methyl 10-undecenoate (Arkema, 75.6 mmol) previously passed over an alumina column, 2 g of acrylonitrile (37.7 mmol) and 150 g of toluene dried on molecular sieves are charged to a 250 ml glass reactor equipped with a condenser and purged with nitrogen. The mixture is heated to 110° C. and 2.4 g of acrylonitrile (45.2 mmol) and 1.9 mg of M71-SiPr catalyst ($2.27 \times 10^{-6}$ mol) dissolved in 5 g of toluene are added via syringes mounted on a syringe driver, over a period of 2 h.

The reaction mixture obtained is analyzed by gas chromatography. The conversion of the methyl 10-undecenoate is 86%. The selectivity toward $C_{11}$ unsaturated nitrile-ester is 79% and the selectivity toward $C_{20}$ unsaturated diester is 21%.

Example 5

Hydrolysis of the Unsaturated $C_{20}$ Diester

The hydrolysis is performed according to the process described in Example 2 to obtain, starting with the C20 methyl diester obtained from Example 4, the unsaturated $C_{20}$ diacid: 10-eicosenedioic acid.

Example 6

Oxidative Cleavage of the Unsaturated $C_{20}$ Diacid

The oxidative cleavage of 10-eicosenedioic acid is performed according to the process described in Example 3, but using butyric acid instead of nonanoic acid. Sebacic acid is obtained in a yield of 35%.

Example 7 (not in Accordance with the Invention)

Homometathesis of methyl 9-decenoate 15 g of methyl 9-decenoate (81 mmol) prepared according to Example 1 of patent US 2011/0 113 679 and purified on alumina, and 150 g of toluene predried over molecular sieves are placed in a 250 ml glass reactor purged with nitrogen. The mixture is heated to 110° C. and 2 mg of M71-SiPr catalyst ($2.4 \times 10^{-3}$ mmol, supplied by the company Umicore) dissolved in 5 ml of toluene are added via a syringe and a syringe driver, over a period of 2 hours. The operating conditions are identical to those of Example 1, except for the absence in the present example of an unsaturated nitrile compound II such as acrylonitrile.

At the end of addition of the catalyst, the reaction mixture is analyzed by GC. The conversion of the methyl 9-decenoate is greater than 99.5%.

Figure 2:
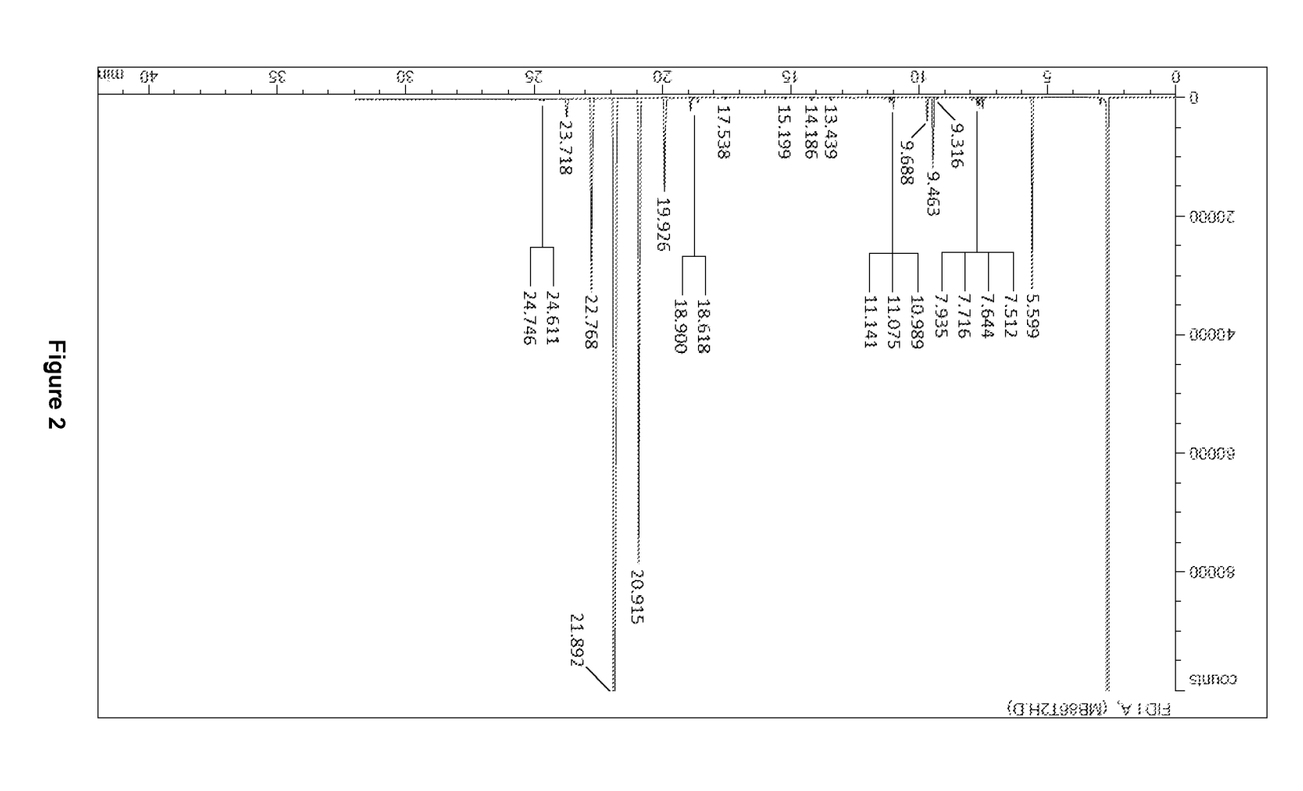
FIG. 2 is a chromatograph illustrating products of the reaction of Example 7.

The GC analysis on the chromatograph of FIG. 2 shows that the selectivity toward methyl 9-octadecenedioate (peak at 21.9 min) does not exceed 68%. Other diesters of different chain lengths (peaks at 18.6; 19.9; 20.9; 22.7; 23.7; 24.6) are formed resulting from isomerization reactions during the metathesis reaction.

The application of an oxidative cleavage reaction to such a reaction product would lead, along with azelaic acid, to a mixture of some 32% of other different diacids and of similar chain lengths, whose separation would be particularly difficult.

The invention claimed is:

1. A process for the conjugate synthesis of a monounsaturated nitrile ester (acid) and of a difunctional carbonyl compound (V), of formula $R_2$—$(CH_2)_n$—$COR'$ in which R' is H or OH, from the same unsaturated fatty compound (I) comprising at least one ester or acid function, respectively, of formula:

in which $R_1$ is H or an alkyl radical comprising from 1 to 4 carbon atoms, $R_2$ is an ester or acid function and n, p and q are integers such that $3 \leq n \leq 13$; $0 \leq p \leq 3$; $0 \leq q \leq 1$, wherein the process comprises:
  a step of cross metathesis cm1 of compound (I) with an unsaturated nitrile compound (II) chosen from: acrylonitrile, fumaronitrile, 2-butenenitrile, 1-butenenitrile, 2-pentenenitrile, 3-pentenenitrile, 4-pentenenitrile and 1-pentenenitrile, in which cm1 is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound (IV) of formula $R_2$—$(CH_2)_n$—HC=CH—$(CH_2)_n$—$R_2$ resulting from the homometathesis of compound (I), and then
  a step of oxidative cleavage cl2 of the double bond respectively of the diester or diacid compound (IV), so as to form a single type of carbonyl compound (V) of formula $R_2$—$(CH_2)_n$—$COR'$ in which R' is H or OH, depending on the operating conditions chosen for the oxidative cleavage cl2,
  in which the cross metathesis step is performed to a degree of conversion in the range from 30% to 90%.

2. The process as claimed in claim 1, in which compound (I) is a fatty acid or an ester of an unsaturated fatty acid of plant or animal origin.

3. The process as claimed in claim 1, wherein the process also comprises a step of hydrogenation of the monounsaturated ester/acid nitrile (III) obtained to form a saturated α,ω-amino ester/acid.

4. The process as claimed in claim 3, in which compound (I) comprises an unsaturation located in the delta x position relative to the ester or acid group R2, which makes it possible to determine the formula of the saturated ω-amino ester/acid.

5. The process as claimed in claim 1, wherein the process also comprises, prior to step cm1, at least one of the following reactions: ethenolysis, butenolysis, propenolysis and/or thermal cracking (pyrolysis) of compound (I), so as to obtain a fatty ester/acid of formula:

6. The process as claimed in claim 1, in which compound (I) is a fatty ester or acid of formula $CH_2$=CH—$(CH_2)_n$—$COOR_3$ in which $R_3$ is H or an alkyl radical comprising from 1 to 11 carbon atoms and n is an integer in the range from 3 to 13.

7. The process as claimed in claim 1, in which the unsaturated nitrile compound (II) used in step cm1 is acrylonitrile.

8. The process as claimed in claim 1, in which the cross metathesis step is performed to a degree of conversion in the range from 40% to 90%.

9. The process as claimed in claim 1, in which the cross metathesis step is performed in the presence of a metathesis catalyst of ruthenium-carbene type chosen from the charged or uncharged catalysts of general formula:

in which:
- a, b, c, d and e are integers, which may be identical or different, with a and b equal to 0, 1 or 2; c, d and e equal to 0, 1, 2, 3 or 4;
- $X_1$ and $X_2$, which may be identical or different, each represent a charged or uncharged and monochelating or polychelating ligand such as halides, sulfate, carbonate, carboxylates, alkoxides, phenoxides, amides, tosylate, hexafluorophosphate, tetrafluoroborate, bis(triflyl)amide, an alkyl, tetraphenylborate and derivatives; $X_1$ or $X_2$ can be bonded to $L_1$ or $L_2$ or to the carbene C so as to form a bidentate or chelate ligand on the ruthenium; and
- $L_1$, $L_2$ and $L_3$, which may be identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether, or a heterocyclic carbene; $L_1$, $L_2$ or $L_3$ can be bonded to the carbene C so as to form a bidentate or chelate ligand, or a tridentate ligand.

10. The process as claimed in claim 9, wherein the catalyst corresponds to the formula:

11. The process as claimed in claim 1, wherein the process comprises an optional intermediate step of hydrolysis between cm1 and cl2 when compound (IV) is a diester, to give the diacid compound (IV).

12. The process as claimed in claim 1, in which the oxidative cleavage step is performed using aqueous hydrogen peroxide solution and/or ozone as oxidizing agent.

13. The process as claimed in claim 1, wherein the oxidative cleavage step is performed under oxidative conditions to give a compound of formula $R_2$—$(CH_2)_n$—COOH, acid ester or diacid.

14. The process as claimed in claim 13, wherein the compound of formula $R_2$—$(CH_2)_n$—COOH is subjected to a hydrolysis to give the diacid when $R_2$ is an ester function.

15. The process as claimed in any one of the preceding claims, wherein the oxidative cleavage step is performed under reductive conditions to give the ester/acid-aldehyde of formula $R_2$—$(CH_2)_n$—CHO.

16. The process as claimed in claim 15, wherein the compound of formula $R_2$—$(CH_2)_n$—CHO is subjected to an additional reduction to give the ester/acid-alcohol of formula $R_2$—$(CH_2)_n$—CH2OH.

17. A process, wherein the process comprises:
starting with the same unsaturated fatty compound (I) comprising, respectively, at least one ester or acid function, of formula:

in which $R_1$ is H or an alkyl radical comprising from 1 to 4 carbon atoms, $R_2$ is an ester or acid function and n, p and q are integers such that $3 \leq n \leq 13$; $0 \leq p \leq 3$; $0 \leq q \leq 1$,
a step of cross metathesis cm1 of compound (I) with an unsaturated nitrile compound (II) chosen from: acrylonitrile, fumaronitrile, 2-butenenitrile, 1-butenenitrile, 2-pentenenitrile, 3-pentenenitrile, 4-pentenenitrile and 1-pentenenitrile, in which cm1 is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound (IV) of formula $R_2$—$(CH_2)_n$—HC=CH—$(CH_2)_n$—$R_2$ resulting from the homometathesis of compound (I),
in which the cross metathesis step is performed to a degree of conversion in the range from 30% to 90%.

18. The process as claimed in claim 1, wherein the process also comprises the hydrogenation of at least part of the symmetrical compound (IV) leading to the corresponding saturated compound (IVs) of formula $R_2$—$(CH_2)_n$—$CH_2$—$CH_2$—$(CH_2)_n$—$R_2$.

19. The process as claimed in claim 17, wherein the process also comprises a step of hydrogenation of the monounsaturated ester/acid nitrile (III) obtained to form a saturated α,ω-amino ester/acid.

20. A process for synthesizing polymer by polymerization using at least one monomer, comprising at least one ω-amino acid, an 107-amino ester, a diacid and/or a diester, manufactured according to a process for the conjugate synthesis of a monounsaturated nitrile ester (acid) and of a difunctional carbonyl compound (V), of formula $R_2$—$(CH_2)_n$—COR' in which R' is H or OH, from the same unsaturated fatty compound (I) comprising at least one ester or acid function, respectively, of formula:

$$R_1\text{—CH}=\text{CH}\text{—}[(CH_2)_q\text{—CH}=\text{CH}]_p\text{—}(CH_2)_n\text{—}R_2 \qquad (I)$$

in which $R_1$ is H or an alkyl radical comprising from 1 to 4 carbon atoms, $R_2$ is an ester or acid function and n, p and q are integers such that $3 \leq n \leq 13$; $0 \leq p \leq 3$; $0 \leq q \leq 1$,
wherein the process comprises:
a step of cross metathesis cm1 of compound (I) with an unsaturated nitrile compound (II) chosen from: acrylonitrile, fumaronitrile, 2-butenenitrile, 1-butenenitrile, 2-pentenenitrile, 3-pentenenitrile, 4-pentenenitrile and 1-pentenenitrile, in which cm1is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound IV of formula $R_2$—$(CH_2)_n$—HC=CH—$(CH_2)_n$—$R_2$ resulting from the homometathesis of compound (I), and then
a step of oxidative cleavage cl2 of the double bond respectively of the diester or diacid compound (IV), so as to form a single type of carbonyl compound (V) of formula $R_2$—$(CH_2)_n$—COR' in which R' is H or OH, depending on the operating conditions chosen for the oxidative cleavage cl2.

21. A polymer wherein the polymer comprises at least one monomer, comprising at least one ω-amino acid, an ω-amino ester, a diacid and/or a diester, manufactured according to a process for the conjugate synthesis of a monounsaturated nitrile ester (acid) and of a difunctional carbonyl compound (V), of formula $R_2—(CH_2)_n—COR'$ in which R' is H or OH, from the same unsaturated fatty compound (I) comprising at least one ester or acid function, respectively, of formula:

$\quad R_1—CH=CH—[(CH_2)_g—CH=]_p—(CH_2)_n—R_2 \quad$ (I)

in which $R_1$ is H or an alkyl radical comprising from 1 to 4 carbon atoms, $R_2$ is an ester or acid function and n, p and q are integers such that $3 \le n \le 13$; $0 \le p \le 3$; $0 \le q \le 1$, wherein the process comprises:
- a step of cross metathesis cm1 of compound (I) with an unsaturated nitrile compound (II) chosen from: acrylonitrile, fumaronitrile, 2-butenenitrile, 1-butenenitrile, 2-pentenenitrile, 3-pentenenitrile, 4-pentenenitrile and 1-pentenenitrile, in which cm1 is brought to partial conversion so as to obtain, and to recover separately, at least the following products: a monounsaturated acid (ester)-nitrile (III) and a symmetrical compound (IV), respectively a diester or diacid comprising a double bond located in the middle of the molecular chain of compound (IV) of formula $R_2—(CH_2)_n—HC=CH—(CH_2)_n—R_2$ resulting from the homometathesis of compound (I), and then
- a step of oxidative cleavage cl2 of the double bond respectively of the diester or diacid compound (IV), so as to form a single type of carbonyl compound (V) of formula $R_2—(CH_2)_n—COR'$ in which R' is H or OH, depending on the operating conditions chosen for the oxidative cleavage cl2.

22. The polymer as claimed in claim 21, wherein the polymer comprises at least one of the following polyamide monomers: 4.6, 4.T, 5.6, 5.9, 5.10, 5.12, 5.13, 5.14, 5.16, 5.18, 5.36, 6, 6.6, 6.9, 6.10, 6.12, 6.13, 6.14, 6.16, 6.18, 6.36, 6.T, 9, 10.6, 10.9, 10.10, 10.12, 10.13, 10.14, 10.16, 10.18, 10.36, 10.T, 11, 12, 12.6, 12.9, 12.10, 12.12, 12.13, 12.14, 12.16, 12.18, 12.36, 12.T, and mixtures thereof.

23. A process for synthesizing polymer by polymerization using at least one monomer, comprising at least one ω-amino acid, an ω-amino ester, a diacid and/or a diester, manufactured according to the process of claim 1.

24. A polymer wherein the polymer comprises at least one monomer, comprising at least one ω-amino acid, an ω-amino ester, a diacid and/or a diester, manufactured according to the process of claim 1.

25. The polymer as claimed in claim 24, wherein the polymer comprises at least one of the following polyamide monomers: 4.6, 4.T, 5.6, 5.9, 5.10, 5.12, 5.13, 5.14, 5.16, 5.18, 5.36, 6, 6.6, 6.9, 6.10, 6.12, 6.13, 6.14, 6.16, 6.18, 6.36, 6.T, 9, 10.6, 10.9, 10.10, 10.12, 10.13, 10.14, 10.16, 10.18, 10.36, 10.T, 11, 12, 12.6, 12.9, 12.10, 12.12, 12.13, 12.14, 12.16, 12.18, 12.36, 12.T, and mixtures thereof.

26. The process as claimed in claim 17, wherein the process also comprises the hydrogenation of at least part of the symmetrical compound (IV) leading to the corresponding saturated compound (IVs) of formula $R_2—(CH_2)_n—CH_2—CH_2—(CH_2)_n—R_2$.

27. The process as claimed in claim 1, wherein the process also comprises a step of hydrogenation of the monounsaturated ester/acid nitrile (III) obtained to form a saturated α,ω-amino ester/acid.

* * * * *